United States Patent
Litvak et al.

(10) Patent No.: US 7,283,877 B1
(45) Date of Patent: Oct. 16, 2007

(54) METHOD OF MEASURING NEURAL RESPONSES

(75) Inventors: Leonid M Litvak, Los Angeles, CA (US); Edward H Overstreet, Valencia, CA (US)

(73) Assignee: Advanced Bionics Corporation, Valencia, CA (US)

( * ) Notice: Subject to any disclaimer, the term of this patent is extended or adjusted under 35 U.S.C. 154(b) by 775 days.

(21) Appl. No.: 10/741,409

(22) Filed: Dec. 19, 2003

Related U.S. Application Data (60) Provisional application No. 60/435,375, filed on Dec. 20, 2002.

(51) Int. Cl.
*A61N 1/00* (2006.01)

(52) U.S. Cl. .............................. 607/67; 607/46; 607/62

(58) Field of Classification Search .................. 607/48, 607/55, 56, 57, 62, 67, 46, 70; 600/544, 600/559
See application file for complete search history.

(56) References Cited

U.S. PATENT DOCUMENTS

| | | | |
|---|---|---|---|
| 3,751,605 A | | 8/1973 | Michelson |
| 4,400,590 A | | 8/1983 | Michelson |
| 4,495,384 A | | 1/1985 | Scott et al. |
| 5,501,703 A | * | 3/1996 | Holsheimer et al. .......... 607/46 |
| 5,603,726 A | | 2/1997 | Schulman et al. |
| 5,626,629 A | | 5/1997 | Faltys et al. |
| 5,938,691 A | | 8/1999 | Schulman et al. |
| 6,067,474 A | | 5/2000 | Schulman et al. |
| 6,078,838 A | | 6/2000 | Rubinstein |
| 6,157,861 A | | 12/2000 | Faltys et al. |
| 6,195,585 B1 | | 2/2001 | Karunasiri et al. |
| 6,205,360 B1 | | 3/2001 | Carter et al. |
| 6,219,580 B1 | | 4/2001 | Faltys et al. |
| 6,249,704 B1 | | 6/2001 | Maltan et al. |
| 6,289,247 B1 | | 9/2001 | Faltys et al. |
| 6,295,467 B1 | | 9/2001 | Kollmeier et al. |
| 6,415,185 B1 | | 7/2002 | Maltan |
| 6,505,078 B1 | * | 1/2003 | King et al. .................... 607/67 |

FOREIGN PATENT DOCUMENTS

WO    WO-03/015863 A2    2/2003

OTHER PUBLICATIONS

Rubinstein et al., "The Neurophysiological Effects of Simulated Auditory Prosthesis Simulation" Second Quarterly Progress Report NO1-DC-6-2111.

van Wieringen, et al., "Comparison of Procedures to Determine Electrical Stimulation Thresholds in Cochlear Implant Users", Ear and Hearing, vol. 22(6), (2001), pp. 528-538.

(Continued)

*Primary Examiner*—Gary Jackson
*Assistant Examiner*—Amanda Patton
(74) *Attorney, Agent, or Firm*—Philip H. Lee; Victoria A. Poissant (57) ABSTRACT

A new method of recording and processing neural responses ("NR") is provided, wherein the method does not assume a linear system response and does not assume a linear response at the interface between electrodes and tissue. The method of the present invention cancels out non-linearities and/or system hysteresis. Other artifacts such as system cross-talk between stimulation and recording circuits are also canceled out. The method provided uses at least two stimulating electrodes simultaneously in one recording step.

18 Claims, 5 Drawing Sheets

OTHER PUBLICATIONS

Overstreet and Faltys inventors for AB-254U; U.S. Appl. No. 10/218,645, filed Aug. 13, 2002; entitled "Cochlear Implant and Simplified Method for Fitting Same".

Faltys inventor for AB-257U; U.S. Appl. No. 10/218,616, filed Aug. 13, 2002; entitled "Bionic Ear Programming System".

Segel, Overstreet, Kruger, and Mishra inventors for AB-313U; U.S. Appl. No. 10/651,653, filed Aug. 29, 2003; entitled "System and Method for Fitting a Cochlear Implant Sound Processor Using Alternative Signals".

Overstreet inventor for AB-362U; U.S. Appl. No. 10/647,372, filed Aug. 25, 2003; entitled "Enhanced Methods for Determining Iso-Loudness Contours for Fitting Cochlear Implant Sound Processors".

Maltan, Miller, and Harrison inventors for AB-376U; U.S. Appl. No. 10/662,615, filed Sep. 30, 2003; entitled "Cochlear Implant Sound Processor with Permanently Integrated Replenishable Power Source".

Overstreet, Litvak, and Faltys inventors for AB-378U; U.S. Appl. No. 10/698,097, filed Oct. 31, 2003; entitled "Multi-Electrode Stimulation to Elicit Electrically-Evoked Compound Action Potential."

Overstreet inventor for AB-379U; U.S. Appl. No. 10/698,098, filed Oct. 31, 2003; entitled "Method and System for Generating a Cochlear Implant Program Using Multi-Electrode Stimulation to Elicit the Electrically-Evoked Compound Action Potential".

Zeng, et al., "Loudness of Simple and Complex Stimuli in Electric Hearing", Annals of Otology, Rhinology & Laryngology, vol. 104 (9), pp. 235-238.

* cited by examiner

METHOD OF MEASURING NEURAL RESPONSES

The present application claims the benefit of U.S. Provisional Patent Application Ser. No. 60/435,375, filed 20 Dec. 2002, which application is herein incorporated by reference in its entirety.

BACKGROUND OF THE INVENTION

The present invention relates to methods of recording a neural response following stimulation of neural tissue. More specifically, the present invention relates to methods for measuring and processing neural responses that minimize stimulus artifacts and system noise.

Modern neural stimulators have the capability of measuring the effectiveness of electrical stimulation of a nerve tissue. This involves delivering a stimulus to a nerve through a stimulating electrode and recording the electrical response, as the nerve depolarizes and repolarizes, using a recording electrode. Such recording and capturing of nerve electrical activity is termed neural response imaging ("NRI").

Obtaining such a neural response ("NR") is important clinically for determining whether stimulation of nerves is occurring at a given stimulus setting and also for determining optimal stimulation parameters for each electrode or electrode configuration.

High quality responses are often difficult to obtain because the neural recordings can be marred by the presence of stimulus artifacts, i.e., the neural recording records the voltage potential of the stimulus pulse rather than the desired NR signal. Another source of recording artifact is cross-talk between the recording circuit and the stimulation circuit. When the recording system is built into a small implantable system, such as an implantable cochlear stimulator or a spinal cord stimulator, the stimulation and recording circuits are necessarily placed very close to each other within the stimulator and, hence, cross-talk can develop between the two circuits.

Several conventional techniques exist for extracting NR, e.g., forward masking, alternating polarity and scaled template methods. These techniques, however, often leave large, residual artifacts, because they assume non-hysteresis and linearity of the system response.

Measurements in saline solution indicate that a large contributory factor to this residual artifact is due to non-linearities of the electrode-tissue interface at the stimulating electrode. This component may be either due to imperfections of the stimulating circuitry or to some poorly understood processes at the electrode-tissue interface.

Accordingly, what is needed is a method of recording and processing neural responses, that largely eliminates this residual artifact component.

SUMMARY OF THE INVENTION

The present invention provides a method of recording and processing neural response using at least two stimulating electrodes, E1 and E2, and a recording electrode. The method comprises: (a) providing Z stimulating electrodes E1, . . . , EZ, and one recording electrode ER, wherein Z is at least two stimulating electrodes; (b) obtaining a recording, RC, using the recording electrode, ER, the RC recording a response to a combination of a simultaneously delivered sub-threshold stimulus pulses, S1 . . . SZ which applied simultaneously together, provide a supra-threshold stimulus amplitude; (c) obtaining separate recordings, R1 . . . RZ, for each stimulating electrode E1 . . . EZ, using substantially identical stimuli, S1 . . . SZ, respectively, as used in step (b), but with each stimuli applied separately to obtain each recording, R1 . . . RZ; (d) recording at least one response, R0, to no stimulation; and (e) processing the obtained recordings to yield an estimated NR in accordance with the relation: $NR = RC - (R1 + \ldots + RZ) + R0*(Z-1)$, wherein Z represents the number of stimulating electrodes used, and R0 is a recording run in which no stimulation is applied.

Applying the generalized relation above, for a two stimulating electrode recording system, the estimated NR is $NR = RC - (R1 + R2) + R0$. For a three stimulating electrode system, the estimated NR is $NR = RC - (R1 + R2 + R3) + R0*2$.

The amplitudes of S1 and S2 may be different, although the pulsewidths can be the same.

In one embodiment of the method of the present invention all of the polarities of S1, S2, and S3 are reversed to obtain the estimated NR and averaged with the NR values obtained using the opposite polarities. The averaged NR provides a more accurate estimate of the NR.

It is a feature of the present invention to provide a recording and processing method that does not assume linearity of response at the electrode-tissue interface.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1A:
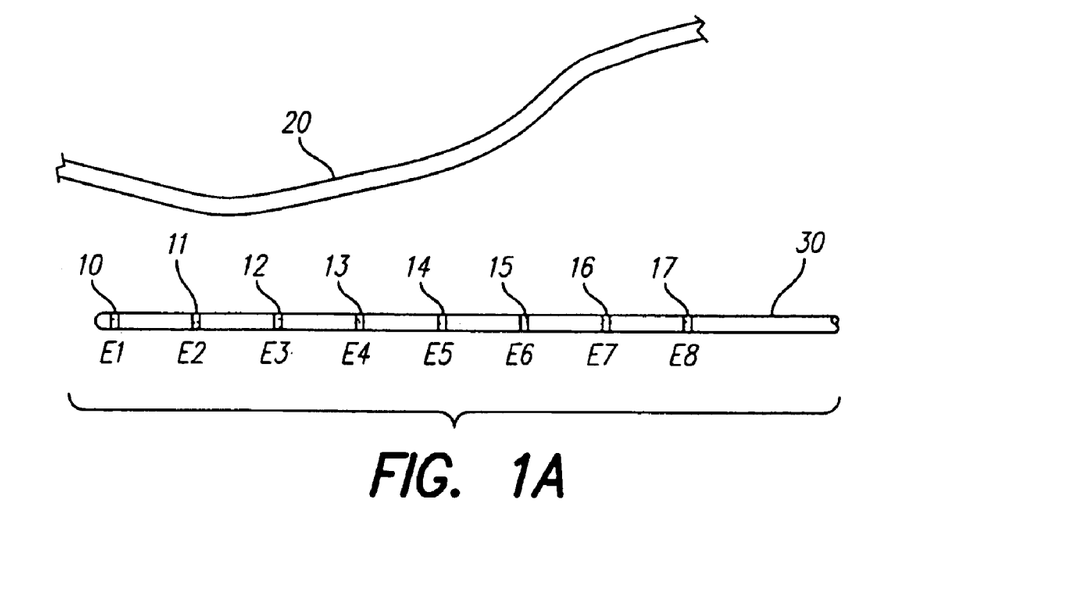
FIG. 1A shows an electrode array used to stimulate a target nerve, wherein at least one of the electrode contacts of the array may be used as a stimulating electrode.

FIG. 1A shows a lead 30 having an electrode array with electrodes E1 . . . E8, which are numbered 10-17. The lead 30 can be attached to an implantable pulse generator ("IPG") (not shown). The IPG may provide independently controllable stimuli to each of the electrodes, 10-17. In addition, the circuitry in the IPG that is attached to each electrode E1 . . . E8 can be switched between stimulation mode and recording mode. As an example, electrode 10 may be selected as a stimulating electrode that is part of the monopolar stimulation circuit that includes the IPG housing which serves as a return electrode. Electrode 11 may be selected as a recording electrode which forms a part of the recording circuit and can record electrical stimulus delivered from electrode 10 and electrical activity along nerve 20. The recorded electrical stimulus is termed a "stimulus artifact," whereas the recorded electrical activity along the nerve is the action potential of the nerve or the neural response (NR).

Figure 1B:
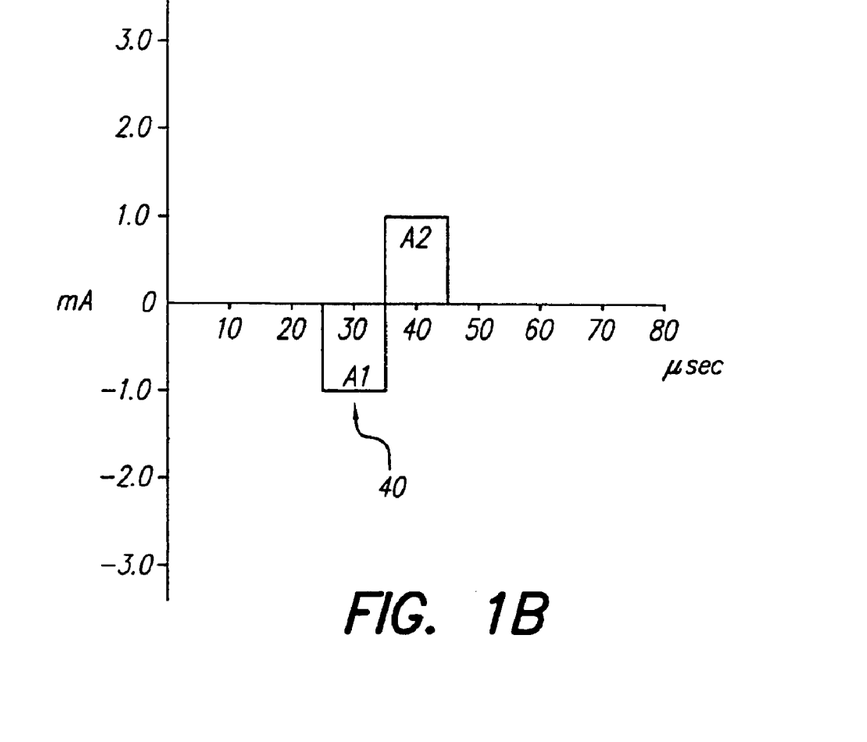
FIG. 1B shows a charged-balanced, biphasic stimulus pulse that can be used to stimulate a nerve.

FIG. 1B shows one example of a biphasic stimulus that may be delivered through electrode 10. The stimulus 40 can consist of two parts, a negative first phase having area A1 and a positive phase having area A2. It is usually the negative phase that causes nerve tissue to depolarize (fire). The stimulus 40 shown is "charged balanced" because the negative area within curve A1 is equal to the positive area A2. While the depolarization of nerve is initiated only by the negative phase of a stimulus, a biphasic, charge-balanced stimulus is often employed because such charge balancing helps reduce electrode corrosion and build-up of charges which can harm surrounding tissue.

When the amplitude and pulsewidth of the stimulus 40 is supra-threshold (a threshold stimulus large enough to depolarize a target nerve), the voltage gradient at some surface point on the nerve 20 will be sufficiently negative as to cause the nerve to depolarize from its resting state and propogate an electrical signal along the length of the nerve. The voltage gradient of this electrical signal propagation can be captured as an NR using the recording electrode 11.

Before discussing the present method of obtaining NRs, it is helpful to understand the components of two exemplary stimulation systems in which the present method for obtaining NRs can be employed.

Figures 1C, 1D:
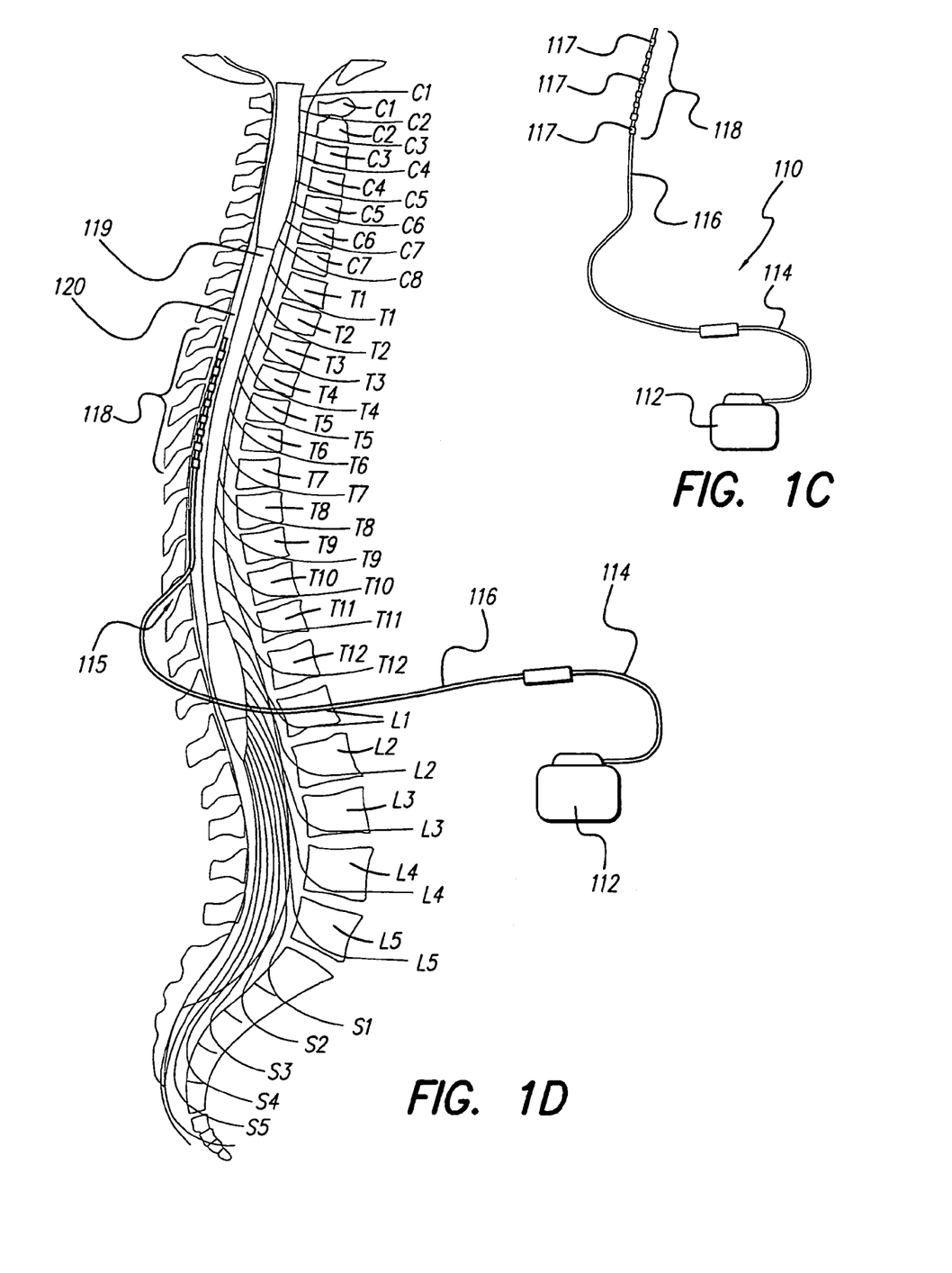
FIG. 1C shows an exemplary stimulation system that may be used to perform spinal cord stimulation (SCS)
FIG. 1D shows the system of FIG. 1C with the electrode array implanted for stimulating spinal cord nerves.

FIGS. 1C and 1D show an exemplary stimulation system 110 that may be used as a spinal cord stimulator (SCS) system for treating chronic pain. In such an application, the lead 116 and, more particularly, the electrode array 118 can be implanted in the epidural space 120 of a patient to be in close proximity to the spinal cord 119.

The system 110 typically comprises an implantable pulse generator (IPG) 112, an optional lead extension 114, an electrode lead 116, having an electrode array 118. The electrode array 118 includes a plurality of electrode contacts 117 (also referred loosely as "electrodes"). The electrode contacts 117 can be arranged, for example, in an in-line array 118 near the distal end of the lead 116. Other electrode array configurations may also be used. The IPG 112 can generate stimulation current pulses that are applied to selected ones of electrodes 117 within the electrode array 118.

A proximal end of the lead extension 114 can be removably connected to the IPG 112 and a distal end of the lead extension 114 can be removably connected to a proximal end of the electrode lead 116. The electrode array 118 is formed on a distal end of the electrode lead 116. The in-series combination of the lead extension 114 and electrode lead 116 carry the stimulation current from the IPG 112 to electrodes of the electrode array 118. The lead extension 114 need not always be used with the neural stimulation system 110, but may be used when the physical distance between the IPG 112 and the electrode array 118 requires its use. Because of the lack of space near the lead exit point 115 where the electrode lead 116 exits the spinal column, the IPG 112 is generally implanted in the abdomen or above the buttocks. The lead extension 114 facilitates locating the IPG 112 away from the lead exit point 115. A more complete description of an SCS system may be found in U.S. Pat. No. 6,516,227, which patent is incorporated herein by reference in its entirety.

It is noted that the SCS system comprising a lead 116, with electrode array 118 connected to an implantable pulse generator (IPG) 112 is a typical set of components for many stimulation systems for treating various ailments. For example, in deep brain stimulation to treat Parkinson's Disease, a system can include those basic components: an IPG, a lead and at least one electrode contact on the lead for delivering stimuli to a target nerve. An external device which is not implanted, e.g., a device programmer, can be used to communicate transcutaneously (through the skin) with the implanted IPG.

Figure 1E:
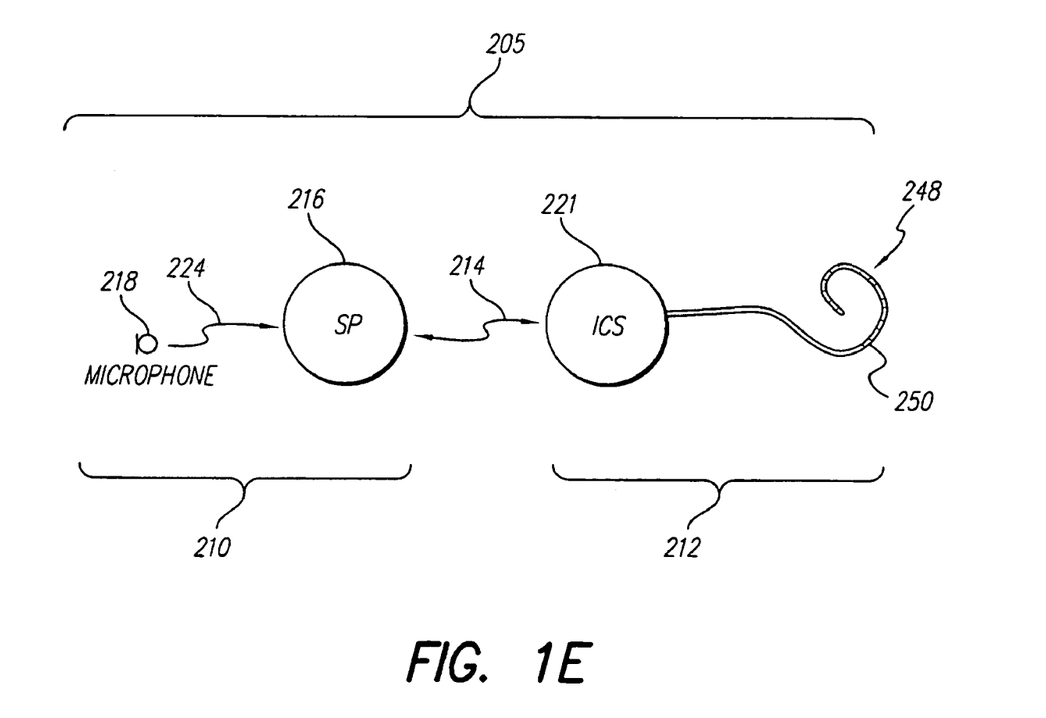
FIG. 1E shows a diagrammatic representation of a cochlear implant system that includes an external speech processor (SP) and an implanted cochlear stimulator (ICS)

FIG. 1E shows a second, exemplary stimulation system which is a cochlear system that can include an external component and an implantable component. FIG. 1E shows a cochlear stimulation system 205 that includes a speech processor portion 210 and a cochlear stimulation portion 212. The speech processor portion 210 includes a speech processor (SP) 216 and a microphone 218. The microphone 218 may be connected directly to the SP 216 or coupled to the SP 216 through an appropriate communication link 224. The cochlear stimulation portion 212 includes an implantable cochlear stimulator (ICS) 221 and an electrode array 248. The electrode array 248 is adapted to be inserted within the cochlea of a patient. The array 248 includes a plurality of electrodes 250, e.g., sixteen electrodes, spaced along the array length and which electrodes are selectively connected to the ICS 221. The electrode array 248 may be substantially as shown and described in U.S. Pat. Nos. 4,819,647 or 6,129,753, both patents incorporated herein by reference. Electronic circuitry within the ICS 221 allows a specified stimulation current to be applied to selected pairs or groups of the individual electrodes included within the electrode array 248 in accordance with a specified stimulation pattern defined by the SP 216.

The ICS 221 and the SP 216 are shown in FIG. 1E as being linked together electronically through a suitable data or communications link 214. In some cochlear implant systems, the SP 216 and microphone 218 comprise the external portion of the cochlear implant system and the ICS 221 and electrode array 248 comprise the implantable portion of the system. Thus, the data link 214 is a transcutaneous (through the skin) data link that allows data, power and control signals to be sent from the SP 216 to the ICS 221. In some embodiments, data and status signals may also be sent from the ICS 221 to the SP 216.

In many systems that stimulate nerve or nerves using an electrical pulse stimulus, it may be desirable to quickly determine the neural response (NR) of a nerve or nerves in response to an applied stimulus. Such a determination of NR, when performed quickly and accurately, can facilitate the optimal setting of the stimulus parameters, e.g, current amplitude and pulsewidth and, moreover, can help characterize the response characteristic of a nerve to various applied stimulus levels. Such information may be useful for setting the upper and lower boundaries of acceptable stimulation levels.

Figure 2:
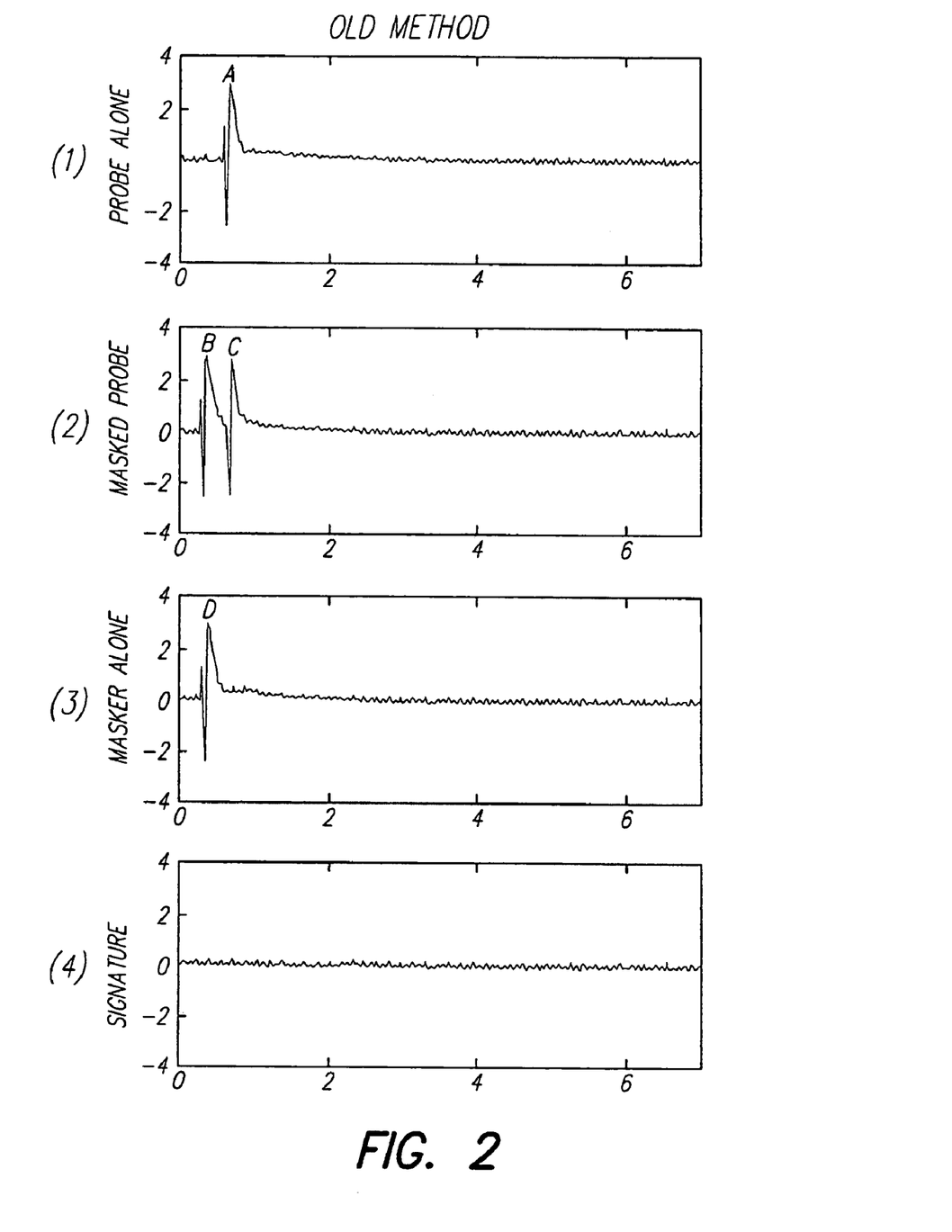
FIG. 2 shows a representation of the conventionally practiced forward masking method.

FIG. 2 shows various response recordings which show stimulus artifacts and neural responses (NRs). The X-axes of the plots are in milliseconds and the Y-axes are in milliamperes. The amplitude of the recorded NR is generally much smaller than of the stimulus response. The recorded stimulus response or the stimulus artifact, swamps the desired NR, as shown in the peaks B and D. The recording electrode 11 records both the stimulus artifact and the NR in peaks B and D and it is therefore necessary to extract the NR from artifacts and noise.

FIG. 2 shows the sequence of recordings, as conventionally practiced, using a forward masking paradigm. In this example, it is assumed that one electrode, for instance, electrode 10 (as seen in FIG. 1a) delivers a stimulus and one electrode, e.g., electrode 11, is the recording electrode.

Recording is activated during the time that one or more stimulus pulses are delivered. Four responses are recorded: as shown in plot (1), a response to the stimulus pulse, which is termed a probe response, Rp; as shown in plot (2), a response to a first stimulus "the masker", followed by a second stimulus pulse, "the probe", which total recorded response is labeled Rmp (response of the masker-probe); as shown in plot (3), a response Rm to a stimulus is labeled "masker alone," which is the total recorded response; and, as shown in plot (4), a response R0 (a signature response) which is the response to no stimulation. R0 includes system noise from cross-talk and system offset. Each of these recorded responses Rp, Rmp, Rm and R0 are obtained in separate (not simultaneous) recordings and can be stored in a database, for example, in computer memory or other digital or analog storage medium to be recalled later for further data processing to obtain an estimate of NR.

An estimate of NR is obtained by applying the formula Rp−(Rmp−Rm)−R0. In FIG. 2, plot (1) shows peak A, which represents Rp=stimulus artifact+NR+system offset/noise. Plot (2) at peak B, represents Rmp=Stimulus artifact+NR+system offset/noise. At peak B, the stimulus applied through electrode 10 is supra-threshold, i.e., the stimulus has sufficient amplitude and pulsewidth to cause the nerve 20 to fire. Second peak C, represents Rmp=stimulus artifact+system offset/noise. This second peak C does not include NR because it is within the relative refractory period of the nerve in which period the nerve cannot be further elicited to fire because the nerve is in a recovery stage. Peak D in plot (3) represents Rm=stimulus artifact+NR+system offset/noise. Plot (4) represents R0 ("signature") which is the system offset/noise over a specific duration of recording time.

As seen in FIG. 2 the X-axis of each plot represents time in milliseconds. The specific example in FIG. 2 depicts a recording duration of about 7 milliseconds. It is understood that the 7 milliseconds is only an example duration and other recording durations may be used.

It can be seen that the when plot (2) is subtracted by plot (3), in other words (Rmp−Rm), the subtraction eliminates the first peak B, leaving only peak C. This subtraction also cancels system offset/noise present in both plot (2) and (3). Thus, the term (Rmp−Rm) theoretically leaves only the residual stimulus artifact. Further substituting into the expression Rp−(Rmp−Rm)−R0 yields plot (1)−stimulus artifact−plot (4) or (stimulus artifact+NR+system offset)−(stimulus artifact)−(system offset), which yields only NR, the estimate of the neural response.

This forward masking technique assumes that the time interval between the onset of the probe pulse, shown as peak B in FIG. 2, and the masker pulse, shown as peak C in FIG. 2, is smaller than the refractory period, such that peak C, "masks out" the response to the peak B.

In practice, the conventional method outlined above can result in sizable residual artifacts in the neural responses. Some possible reasons why the method of cancellation is imperfect include the fact that the state of the system at the outset of the probe alone presentation differs from the state of the system during the probe presentation after the masker. Specifically, the state of the system during the time of peak C of plot (2) may not be the same as in peak A of plot (1) which means that the subtraction does not cancel the stimulus artifact as intended. Another reason is that internal capacitors and/or the electrode-fluid interface accumulate charge during the masker presentation (first peak B in plot (2)) and a further reason is that there are non-linearities and/or hysteresis present in the IPG circuits and the electrode-tissue interface. Peak C may include some state differences caused by non-linear system state changes after peak B. These non-linear effects are not accommodated in the conventional forward masking technique.

An aspect of the present invention provides a method for finding NR which does not assume a linear system response. Referring back to FIG. 1, which shows the electrode array, the method of the present invention involves making a recording RC using recording electrode, ER, while presenting two stimulus pulses, S1 and S2, simultaneously at any two stimulating electrodes (electrode contacts), for example, E1 and E2, respectively, such that the combination of S1 and S2 provides a supra-threshold stimulus, although S1 or S2 taken alone are sub-threshold, i.e, will not cause the nerve to be captured (stimulated). "RC" signifies that the recording is a response from a combination of at least two stimulus applied simultaneously from two different electrodes. The amplitudes of S1 and S2 may be different or they may be same, although the pulsewidths should be the same.

In a separate run, recording, R1, is also made at recording electrode ER while presenting a stimulus pulse, S1 at E1, wherein S1 is sub-threshold, when presented by itself, so that no NR is obtained, only the stimulus artifact of S1. In another separate run, recording, R2, is made using recording electrode ER by presenting S2 at E2, wherein S2 is a sub-threshold stimulus, when presented by itself, so that no NR is obtained, only the stimulus artifact of S2. A recording R0 is made using the recording electrode ER, where no stimulus is provided on any stimulating electrode. This R0 recording provides a system offset recording which includes noise and system cross-talk.

Figure 3:
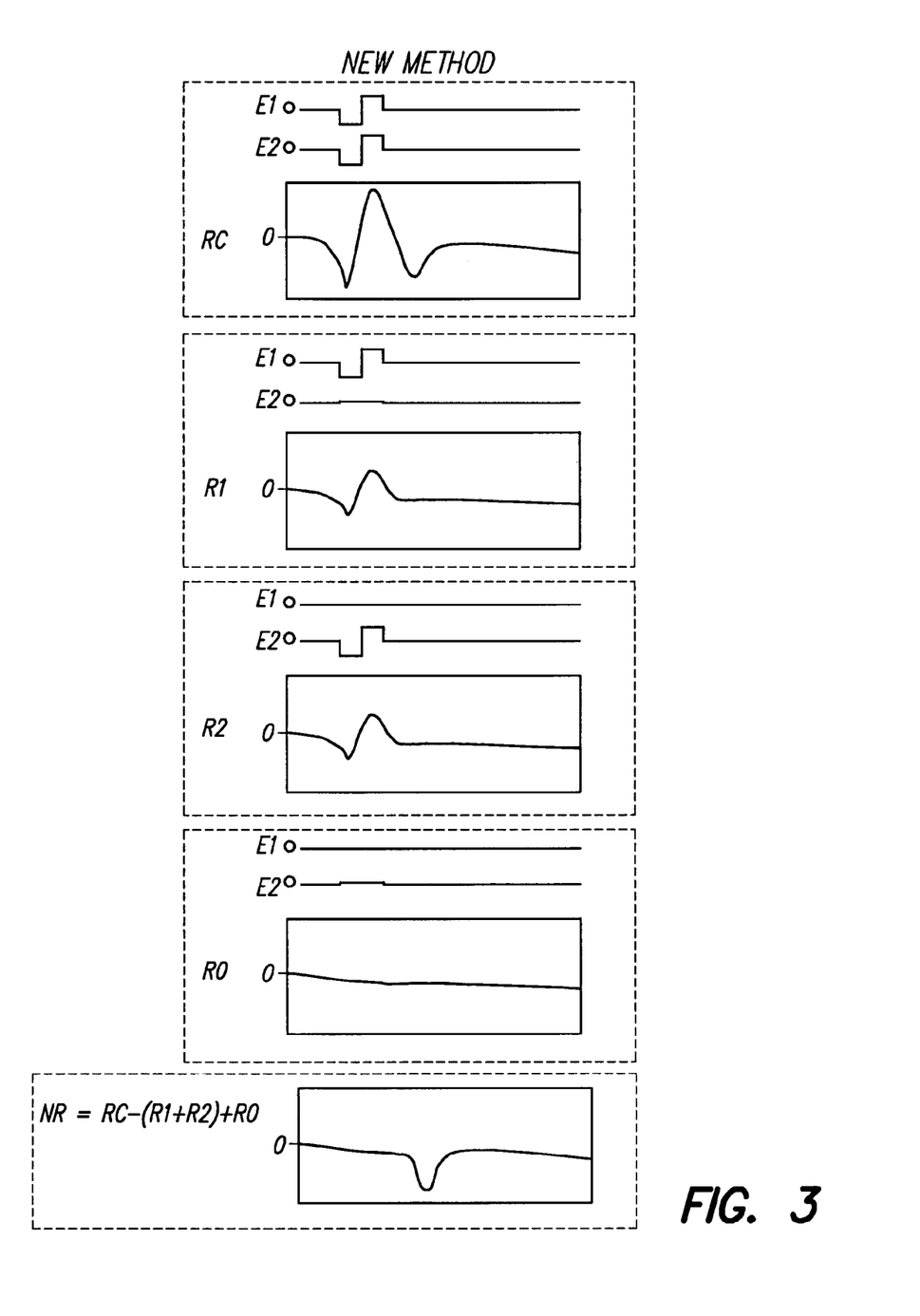
FIG. 3 shows exemplary recordings used to measure a neural response as taught by the findings of the present disclosure.

It is emphasized that RC, R1, R0 and R2 may be recorded in any sequence. Moreover, each of the recordings can be performed more than once to yield averaged results which are more accurate than a single recording. Exemplary recordings for RC, R1, R2 and R0 are shown in FIG. 3.

Finally, the four sets of recording may be used to derive an estimate NR using the relation:

Estimate of NR=RC−(R1+R2)+R0, where RC is the combination recording when at least two stimulating electrodes E1 and E2 are delivering stimulus S1 and S2, respectively, and R1 is the recording when the first stimulating electrode E1 delivers a stimulus alone, R2 is the recording when the second electrode E2 delivers a stimulus alone, and R0 is the recording when no stimulus is delivered by any stimulating electrode. All recordings can be performed via a single recording electrode ER. An exemplary estimate of NR using the relation NR=RC−(R1+R2)+R0 is shown in FIG. 3.

TABLE 1

Two Stimulating Electrode Example of Present Method for obtaining NR

| Steps of the Method | E1-stimulus applied | E2-stimulus applied | Recording Produced or Result using recording electrode ER |
|---|---|---|---|
| RC | S1 | S2 | NR + SA1 + SA2 + Offset/noise |

TABLE 1-continued

Two Stimulating Electrode Example of Present Method for obtaining NR

| Steps of the Method | E1-stimulus applied | E2-stimulus applied | Recording Produced or Result using recording electrode ER |
|---|---|---|---|
| R1 | S1 | — | SA1 + Offset/noise |
| R2 | — | S2 | SA2 + Offset/noise |
| R0 | — | — | Offset/noise |
| RC − (R1 + R2) + R0 | | | Estimated NR |

Table 1 provides a two stimulating electrode example of the method of the present invention. Table 1 shows the stimuli delivered for each recording, RC, R1, R2 and R0, and what each of the recordings represents. The last step takes the four recordings and applies the relation NR=RC−(R1+R2) +R0. It can be seen that the method of the present invention cancels out non-linearities and hysteresis in the system.

A further refinement of the method of the present invention is to make a number of runs for at least one of the recordings, RC, R1, R2, R0, and to obtain an averaged result. Such an averaged result can provide a more accurate estimate of NR. Alternatively, a number of NRs may be obtained and an averaged NR may be obtained, which should also provide a more accurate estimate of NR.

In another embodiment of the present invention, the above steps can be repeated except that in the second set of recordings, S1', S2' may be stimuli of opposite polarities compared to the S1, S2 in the first set of recordings. In other words, the stimulus current will be delivered in each stimulation circuit in the opposite direction (or polarity) in the second set of recordings. For example, when two stimulating electrodes, E1 and E2, are used, each also must be connected in a circuit to a return or indifferent electrode. When the return electrode is very close in location to E1, for example, E3 on the same electrode array, that provides a bipolar electrode configuration. If the return electrode, however, is the case or housing of an IPG, that provides a monopolar electrode configuration. The resulting NRs from the sets of recordings can be taken and averaged together to provide a more accurate measure of the estimated NR. This second embodiment can be combined with the concept of averaging the result of an individual recording run, RC, R1, R2 or R0.

As a further embodiment of the present method, it can be seen that the method described can be generalized to more than two stimulating electrodes, such that there may be E1 . . . EZ stimulating electrodes and a recording electrode ER in an electrode array. For instance, if three stimulating electrodes are used, E1, E2, and E3, located in an electrode array, a fourth electrode E4 located on the same electrode array can be used as the recording electrode ER. Alternatively, ER may be chosen to be an electrode on a different electrode array that does not include the stimulating electrodes E1, E2 or E3.

In a three stimulating electrode configuration, the following steps can be taken, as one example, in accordance with the present invention:

Step 1: Obtain recording RC (combination stimuli) by simultaneously delivering stimuli S1 (at E1)+S2 (at E2)+S3 (at E3), wherein S1, S2, S3 are all sub-threshold stimuli when each are taken alone, but when all three stimuli are added together, the combination stimulus provides a supra-threshold stimulus;

Step 2: Obtain recording R1 for a single stimulus S1 delivered alone through electrode E1;

Step 3: Obtain recording R2 for a single stimulus S2 delivered alone through electrode E2;

Step 4: Obtain recording R3 for a single stimulus S3 delivered alone through electrode E3;

Step 5: Obtain R0, while no stimulus is delivered through any stimulating electrode; and optionally, Step 6: Obtain another R0', while no stimulus is delivered through any stimulating electrode.

Step 7: Estimate NR by applying the relation:

Estimated NR=RC+(R1+R2+R3)+R0+R0'

TABLE 2

Example of Present Method Using Three Stimulating Electrodes

| Step of Method | E1 | E2 | E3 | Recording Produced or Result |
|---|---|---|---|---|
| RC | S1 | S2 | S3 | NR + SA1 + SA2 + SA3 + Offset/noise |
| R1 | S1 | — | — | SA1 + Offset/noise |
| R2 | — | S2 | — | SA2 + Offset/noise |
| R3 | — | — | S3 | SA3 + Offset/noise |
| R0 | — | — | — | Offset/noise |
| R0' | — | — | — | Offset/noise |
| RC − (R1 + R2 + R3) + R0 + R0' | | | | NR |

Table 2 provides an example sequence of steps taken in accordance with the present invention in which three electrodes are stimulating electrodes. It is emphasized that the steps for obtaining RC, R1, R2, R3, R0 and R0' do not need to be in the order as shown in the Table 2, but may be obtained in any sequence. In addition, R0+R0' may be substituted by R0*2, so that only one recording of R0 is taken. Additionally, each recording step, RC, R1, R2, R3, R0, R0' may be taken more than once in order to obtain an averaged recording, which will provide more accurate results for the final estimated value of NR.

In summary, it can be seen that the method of the present invention can be generalized for any number of stimulating electrodes, such that: the estimated NR=RC−(R1+ . . . +RZ)+R0 + . . . +R0'$_{z-1}$, or alternatively, NR=RC−(R1+ . . . +RZ)+R0*(Z−1), where Z, which is at least 2, is the number of stimulating electrodes used, and R0 is a recording run in which no stimulation is applied at any stimulating electrode. As shown in Table 2, R0 and R0' are recording runs where no stimulation is applied. A minor modification is to use a single R0 run and use a correct multiplier (Z−1) to eliminate as many Offset/noise as necessary. However, more accurate results for NR can be obtained by taking as many separate R0 runs as needed, or even additional runs to obtain an averaged R0 value.

One embodiment of the present method uses the same duration of recordings for RC, R1 . . . RZ, and R0, thereby making numerical functions such as subtraction, addition, multiplication and division easier to perform.

S1 . . . SZ may be essentially identical sub-threshold stimuli, although it is possible to use stimuli that are of different amplitudes. The shapes of the stimuli preferably are consistent, however. For instance, they may all be monophasic stimuli or they may all be biphasic stimuli. If biphasic, the first phase of each stimuli may have a negative polarity. The biphasic stimuli are preferably charged-balanced. However, the pulsewidths of each stimuli S1 . . . SZ should be the same.

As shown the method of the present invention may be used with a wide variety of stimulating systems. The exemplary SCS system, shown in FIGS. 1C and 1D, includes an IPG and a lead with one electrode contact or an array of electrodes. With such a system, all of the recording and processing may be performed by electronic circuitry, including a microprocessor that is contained inside the implanted device, e.g., the IPG. It is also possible to have the IPG uplink recorded runs, RC, R1 . . . RZ, R0, contained in memory inside the IPG to an external device with a processing capability to determined the final estimated NR.

A second exemplary stimulation system is a cochlear implant system that may have two component parts. In such a system the external speech processor, SP, which may be in the form of a behind-the-ear (BTE) device, can contain a processor and memory that can record the runs, RC, R1 . . . RZ, R0, store the recorded runs, and process these recordings to obtain an estimated NR.

In general, the recording runs may be digital, sampled data and stored in memory as arrays of datapoints, e.g., (time; recorded signal amplitude). Use of data arrays can facilitate the manipulation and processing of sets of recording runs, RC, R1 . . . RZ, and R0, in order to obtain an estimated NR.

While the invention herein disclosed has been described by means of specific embodiments and applications thereof, numerous modifications and variations could be made thereto by those skilled in the art without departing from the scope of the invention set forth in the claims.

What is claimed is:

1. A method of recording and processing neural response (NR), the method comprising:
   (a) providing a stimulating electrode, E1, and a stimulating electrode, E2, and a recording electrode ER;
   (b) recording RC, in response to a combination of a first, sub-threshold stimulus pulse, S1 at E1, having amplitude A and a second, sub-threshold stimulus pulse, S2 at E2, having amplitude B, wherein S1 and S2 are applied simultaneously and, when added together, provide a supra-threshold stimulus amplitude C;
   (c) recording R1, in response to a sub-threshold stimulus pulse, S1 delivered through electrode E1;
   (d) recording R2, in response to a sub-threshold stimulus pulse, S2 delivered through electrode E2;
   (e) recording R0, in response to no stimulation at any stimulating electrodes; and
   (f) processing the recordings to yield an estimated NR in accordance with the relation: NR=RC−(R1+R2)+R0, wherein the steps (b), (c), (d) and (e) may be performed in any order.

2. The method of claim 1, wherein the duration of each of the recordings RC, R1, R2 and R0 is approximately the same, thereby making subtraction and addition of recording data RC, R1, R2 or R0 easier by having the same number of data points in each recording.

3. The method of claim 1, wherein S1 and S2 are essentially identical stimulus with respect to shape, pulse-width and amplitude.

4. The method of claim 1, wherein the at least two stimulating electrodes E1 and E2 stimulate a cochlear nerve.

5. The method of claim 1, wherein the at least two stimulating electrodes E1 and E2 stimulate a spinal cord nerve.

6. The method of claim 1, wherein S1 and S2 are charged-balance stimuli.

7. The method of claim 1, wherein at least one of the recordings, RC, R1, R2 or R0 is performed at least twice and then averaged to provide an averaged response recording that is more accurate than a single recording.

8. The method of claim 1, wherein each step (b), (c), (d) and (e) are performed twice in two separate runs, but with stimulus S1 and S2 applied having opposite polarities during the two runs, and the final NR estimate an average of the two NR estimates obtained from the two runs.

9. The method of claim 8, wherein at least one of the recordings, RC, R1, R2 or R0 is performed at least twice, using the same polarity stimulus, and then averaged to provide an averaged response recording that is more accurate than a single recording.

10. A method of recording and processing NR, the method comprising:
   (a) providing Z stimulating electrodes E1, . . . , EZ, and one recording electrode ER, wherein Z is at least three stimulating electrodes;
   (b) obtaining a recording, RC, using the recording electrode, ER, the RC recording a response to a combination of a simultaneously delivered sub-threshold stimulus pulses, S1 . . . SZ, which applied simultaneously together, provide a supra-threshold stimulus amplitude;
   (c) obtaining separate recordings, R1 . . . RZ for each stimulating electrode E1 . . . EZ, using substantially identical stimuli, S1 . . . SZ, respectively, as used in step (b), but with each stimuli applied separately to obtain each recording, R1 . . . RZ;
   (d) recording at least one R0 recording to no stimulation; and
   (e) processing the obtained recordings to yield an estimated NR in accordance with the relation: NR=RC−(R1+ . . . +RZ)+R0*(Z−1),
   wherein Z is at least three and represents the number of stimulating electrodes used, and R0 is a recording run in which no stimulation is applied.

11. The method of claim 10, in which R0 is an averaged value from at least two separate runs.

12. The method of claim 10, wherein S1, . . . SZ, are essentially identical stimulus with respect to shape, pulse-width and amplitude.

13. The method of claim 10, wherein the stimulating electrodes E1 through EZ stimulate a cochlear nerve.

14. The method of claim 10, wherein the stimulating electrodes E1 through EZ stimulate a spinal cord nerve.

15. the method of claim 10, wherein all stimuli presented S1 . . . SZ are charged-balance stimuli.

16. The method of claim 10, wherein at least one of the recordings, R0, RC, and R1 through RZ, is performed at least twice and then averaged to provide an averaged response recording.

17. The method of claim 10, wherein each steps (b), (c), (d) and (e) are performed twice in two separate runs, but with stimuli S1 . . . SZ applied having opposite polarities in the two runs and the final NR estimate is an average of the NR estimates obtained from the two runs, wherein the stimulus amplitudes, S1 . . . SZ, in the two runs may be identical or different between the two runs.

18. The method of claim 17, wherein at least one of the recordings, RC, R0 or R1 . . . RZ is performed at least twice, using the same polarity stimulus, and then averaged to provide an averaged response recording that is more accurate than a single recording.

* * * * *